United States Patent
Creemer et al.

(10) Patent No.: US 9,193,750 B2
(45) Date of Patent: Nov. 24, 2015

(54) PROCESS FOR THE PREPARATION OF CERTAIN TRIARYL RHAMNOSE CARBAMATES

(71) Applicant: Dow AgroSciences LLC, Indianapolis, IN (US)

(72) Inventors: Lawrence C. Creemer, Greenfield, IN (US); Carl DeAmicis, Indianapolis, IN (US); Gary D. Crouse, Noblesville, IN (US); Peter Borromeo, Fishers, IN (US)

(73) Assignee: Dow AgroSciences LC, Indianapolis, IN (US)

( * ) Notice: Subject to any disclaimer, the term of this patent is extended or adjusted under 35 U.S.C. 154(b) by 0 days.

(21) Appl. No.: 14/288,418

(22) Filed: May 28, 2014

(65) Prior Publication Data

US 2014/0378674 A1    Dec. 25, 2014

Related U.S. Application Data

(60) Provisional application No. 61/837,203, filed on Jun. 20, 2013.

(51) Int. Cl.
*C07H 1/00* (2006.01)
*C07H 13/12* (2006.01)
*C07H 15/04* (2006.01)

(52) U.S. Cl.
CPC .................. *C07H 13/12* (2013.01); *C07H 1/00* (2013.01); *C07H 15/04* (2013.01)

(58) Field of Classification Search
None
See application file for complete search history.

(56) References Cited

U.S. PATENT DOCUMENTS

2009/0209476 A1    8/2009    Crouse et al.

OTHER PUBLICATIONS

International Search Report and Written Opinion for PCT/US2014/039695 mailed Oct. 1, 2014.

*Primary Examiner* — Patrick Lewis
(74) *Attorney, Agent, or Firm* — Carl D. Corvin

(57) ABSTRACT

Triaryl rhamnose carbamate insecticides are prepared from triaryl acyl azides and tetrahydropyran-2-ols in good yield without the use of a hydride base.

6 Claims, No Drawings

PROCESS FOR THE PREPARATION OF CERTAIN TRIARYL RHAMNOSE CARBAMATES

CROSS REFERENCE TO RELATED APPLICATIONS

This application claims the benefit of U.S. Provisional Patent Application Ser. No. 61/837,203 filed Jun. 20, 2013, the entire disclosure of which is hereby expressly incorporated by reference.

BACKGROUND OF THE INVENTION

The present invention concerns an improved process for preparing certain triaryl rhamnose carbamates.

U.S. Pat. No. 8,178,658 describes, inter alia, certain triaryl rhamnose carbamates and their use as insecticides. One of the methods used to prepare such triaryl compounds is by way of a the following 2 step process

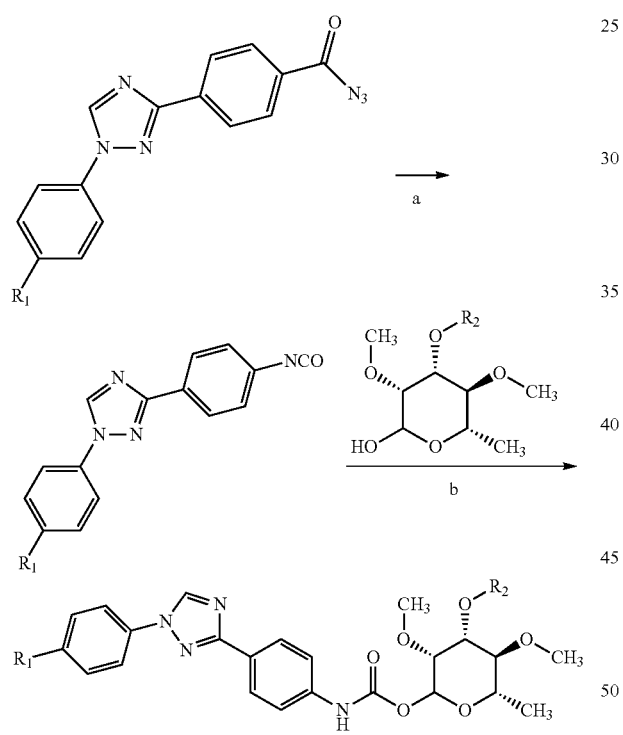

wherein
$R_1$ represents $(C_1-C_6)$haloalkyl or $(C_1-C_6)$haloalkoxy, and
$R_2$ represents $(C_1-C_6)$alkyl, $(C_2-C_6)$alkenyl, or $(C_2-C_6)$alkynyl,
in which a triaryl acyl azide is converted to an isocyanate followed by reaction with a tetrahydropyran-2-ol and a strong base to give the triaryl rhamnose carbamate pesticide. However, the reaction of the triaryl carbamate with the tetrahydropyran-2-ol requires the use of a strong hydride base, provides an anomeric mixture of alpha and beta products, and gives rise to urea and aniline by-products. It would be desirable to have a process in which the triaryl acyl azide and the tetrahydropyran-2-ol could be coupled in good yield without the use of a hydride base. It would also be desirable to reduce the amount of by-product formation and to provide a predominance of the preferred anomeric isomer.

SUMMARY OF THE INVENTION

The present invention provides such conditions. Thus, the present invention concerns a process for preparing certain triaryl rhamnose carbamates of the Formula (I),

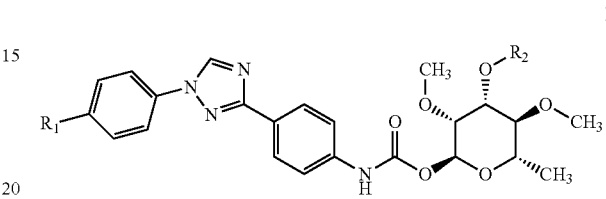

I wherein
$R_1$ represents $(C_1-C_6)$haloalkyl or $(C_1-C_6)$haloalkoxy, and
$R_2$ represents $(C_1-C_6)$alkyl, $(C_2-C_6)$alkenyl, or $(C_2-C_6)$alkynyl,
which comprises
a) rearranging a triaryl acyl azide of Formula (II)

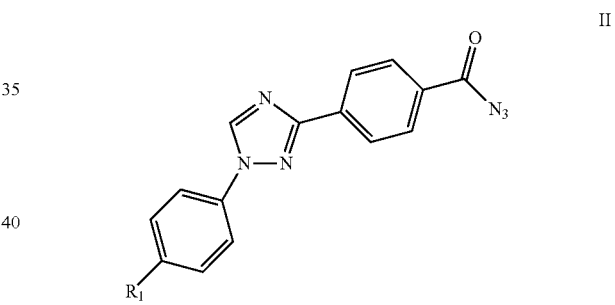

II wherein
$R_1$ is as previously defined,
to an isocyanate of Formula (III)

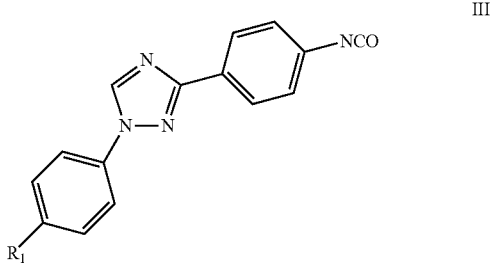

III wherein
$R_1$ is as previously defined,
by heating at a temperature of about 60° C. to about 110° C. in an anhydrous aprotic solvent, and b) contacting the isocyanate of Formula (III) with a tetrahydropyran-2-ol of Formula (IV)

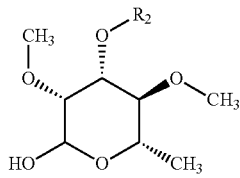

IV wherein
$R_2$ is as previously defined,
in a polar aprotic solvent in the presence of cesium carbonate.

DETAILED DESCRIPTION OF THE INVENTION

Throughout this document, all temperatures are given in degrees Celsius, and all percentages are weight percentages unless otherwise stated.

The term "alkyl", as well as derivative terms such as "haloalkyl" and "haloalkoxy", as used herein, include within their scope straight chain, branched chain and cyclic moieties. Thus, typical alkyl groups are methyl, ethyl, propyl, butyl, pentyl, hexyl, 1-methylethyl, 1,1-dimethylethyl, 1-methylpropyl, 2-methylpropyl, cyclopropyl, cyclobutyl, cyclopentyl and cyclohexyl. The term "alkenyl", as used herein, means an acyclic, unsaturated (at least one carbon-carbon double bond), branched or unbranched substituent consisting of carbon and hydrogen, for example, vinyl, allyl, butenyl, pentenyl or hexenyl. The term "alkynyl", as used herein, means an acyclic, unsaturated (at least one carbon-carbon triple bond), branched or unbranched substituent consisting of carbon and hydrogen, for example, ethynyl, propargyl, butynyl, pentynyl or hexynyl. The terms "haloalkyl" and "haloalkoxy" includes alkyl or alkoxy groups substituted with from one to the maximum possible number of halogen atoms, all combinations of halogens included. The term "halogen" or "halo" includes fluorine, chlorine, bromine and iodine, with fluorine being preferred.

The present invention concerns a process for preparing certain triaryl rhamnose carbamates of the Formula (I),

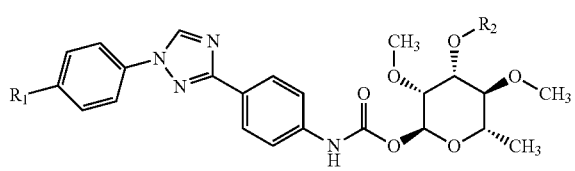

I wherein
$R_1$ represents $(C_1-C_6)$haloalkyl or $(C_1-C_6)$haloalkoxy, and
$R_2$ represents $(C_1-C_6)$alkyl, $(C_2-C_6)$alkenyl or $(C_2-C_6)$alkynyl, by rearranging a triaryl acyl azide of Formula (II)

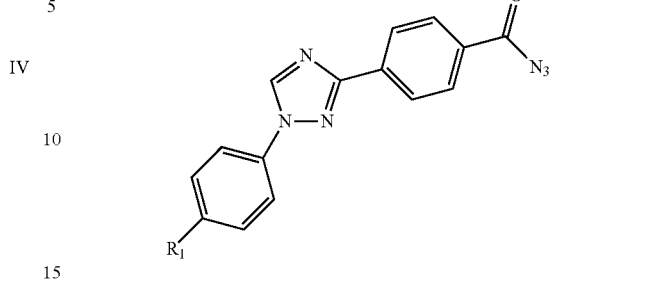

II wherein
$R_1$ is as previously defined,
to an isocyanate of Formula (III)

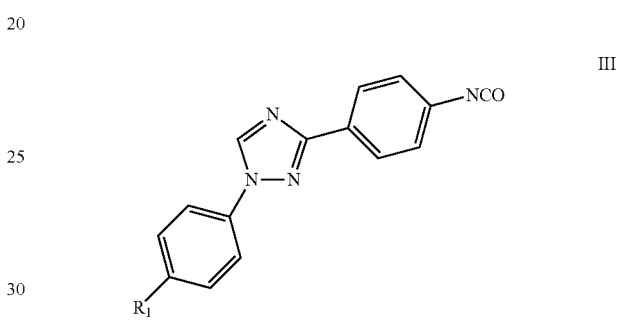

III wherein
$R_1$ is as previously defined,
and by contacting the isocyanate of Formula (III) with a tetrahydropyran-2-ol of Formula (IV)

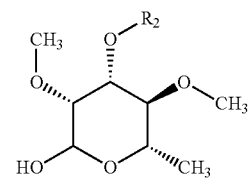

IV wherein
$R_2$ is as previously defined,
in good yield without having to use a hydride base. This is accomplished by heating the acyl azide in an anhydrous aprotic solvent at a temperature from about 60° C. to about 110° C. to form an isocyanate (Curtius rearrangement), followed by reaction with the tetrahydropyranol in a polar aprotic solvent in the presence of cesium carbonate. The tetrahydropyranols of Formula (IV) consist of approximately a 3:1 mixture of C2 anomers, with the 2R anomer predominating. The initial carbamate product, therefore, consists of a mixture of C2-anomers, formed in the same ratio. Under the conditions described above, this initially formed isomeric mixture undergoes equilibration, leading ultimately to a product that is greater than or equal to 98 percent of the (2S) configuration.

$R_1$ is preferably a $(C_1-C_2)$fluoroalkoxy group; and $R_2$ is preferably $CH_2CH_3$, $CH_2CH_2CH_3$ or $CH_2CH=CH_2$.

The triaryl acyl azides of Formula I are known from U.S. Pat. No. 8,178,658.

The rearrangement of the acyl azide to the isocyanate is conducted by heating the acyl azide in an anhydrous aprotic solvent at a temperature from about 60° C. to about 110° C. to form an isocyanate. The reaction is conducted in a wide variety of aprotic solvents including, for example, aromatic hydrocarbons, e.g., benzene, toluene, or xylenes; and polar aprotic solvents, e.g., ethers like tetrahydrofuran, 2-methyltetrahydrofuran and methyl tert-butyl ether, and nitriles like acetonitrile and butyronitrile, and mixtures thereof. Currently, it is preferred if toluene, acetonitrile, 2-methyltetrahydrofuran and mixtures thereof are used. The aprotic solvent should be as anhydrous as possible to avoid hydrolysis of the product isocyanate and the formation of by-product ureas.

In a typical reaction, the triaryl acyl azide is dissolved in the anhydrous aprotic solvent and heated at about 100° C. until the reaction is completed. It is most convenient to perform the rearrangement in an anhydrous aprotic solvent that is suitable for the reaction with the tetrahydropyran-2-ol so that the isocyanate can be used without isolation.

In the second step, the isocyanate is reacted with the tetrahydropyran-2-ol. Approximately a 1:1 molar ratio of the isocyanate and the tetrahydropyran-2-ol may be used, however, molar ratios of about 1.2:1 to about 1:1.2 may also be used. Suitable examples of tetrahydropyran-2-ols include (3R,4R,5S,6S)-3,4,5-trimethoxy-6-methyltetrahydro-2H-pyran-2-ol, (3R,4R,5S,6S)-4-ethoxy-3,5-dimethoxy-6-methyltetrahydro-2H-pyran-2-ol, (3R,4R,5S,6S)-3,5-dimethoxy-6-methyl-4-propoxytetrahydro-2H-pyran-2-ol, and (3R,4R,5S,6S)-4-(allyloxy)-3,5-dimethoxy-6-methyltetrahydro-2H-pyran-2-ol. Currently, it is preferred if (3R,4R,5S,6S)-3,5-dimethoxy-6-methyl-4-propoxytetrahydro-2H-pyran-2-ol or (3R,4R,5S,6S)-4-(allyloxy)-3,5-dimethoxy-6-methyltetrahydro-2H-pyran-2-ol is used.

In the second step, isocyanate is contacted with the tetrahydropyran-2-ol in a polar aprotic solvent which includes amides, like N,N-dimethylformamide, N,N-dimethylacetamide or N-methyl-2-pyrrolidinone, sulfoxides, like dimethyl sulfoxide, esters, like ethyl acetate, ethers, like tetrahydrofuran, 2-methyl-tetrahydrofuran and dimethoxyethane, and nitriles, like acetonitrile, butyronitrile and benzonitrile. Nitriles, particularly acetonitrile, are preferred. The polar aprotic solvent should be as anhydrous as possible to avoid hydrolysis of the isocyanate and the formation of byproduct ureas. The polar aprotic solvent can be used in mixtures with other aprotic solvents such as aromatic hydrocarbons, like toluene. Mixtures like toluene and acetonitrile are particularly suitable for both steps when the isocyanate from step a) is used without isolation.

The second reaction is run in the presence of cesium carbonate, usually in the presence of from about 0.05 to about 1 equivalents, with from about 0.1 to about 0.5 equivalents being preferred.

The second reaction is conducted at a temperature from about 0° C. to about 90° C., with a temperature from about 0° C. to about 35° C. being preferred. The tetrahydropyran-2-ol IV normally exists as a mixture of anomeric forms, α and β. During the course of the reaction with the isocyanate, both the α and β anomers of the carbamate are initially formed. With continued stirring after the isocyanate has been converted entirely into the mixture of carbamates, further equilibration occurs, resulting ultimately in >98% formation of the α anomer.

In a typical reaction, the tetrahydropyran-2-ol and the cesium carbonate in the anhydrous polar aprotic solvent are added to the isocyanate in the anhydrous aprotic solvent from step a). It is also possible to perform the rearrangement of step a) in the presence of the tetrahydropyran-2-ol, to form an anomeric mixture of carbamates. In such case, the isocyanate is prepared and used in situ. The later addition of the cesium carbonate helps to drive carbamate formation to completion and to drive equilibration to the desired a anomer. The reaction is stirred at room temperature until the reaction and equilibration are completed. The reaction mixture is filtered to remove solids, the solvent is evaporated and the isolated product purified by conventional techniques such as flash chromatography or recrystallization.

The following examples are presented to illustrate the invention.

EXAMPLES

Example 1

Preparation of (2S,3R,4R,5S,6S)-3,5-dimethoxy-6-methyl-4-propoxytetrahydro-2H-pyran-2-yl(4-(1-(4-(perfluoroethoxy)phenyl)-1H-1,2,4-triazol-3-yl)phenyl)carbamate

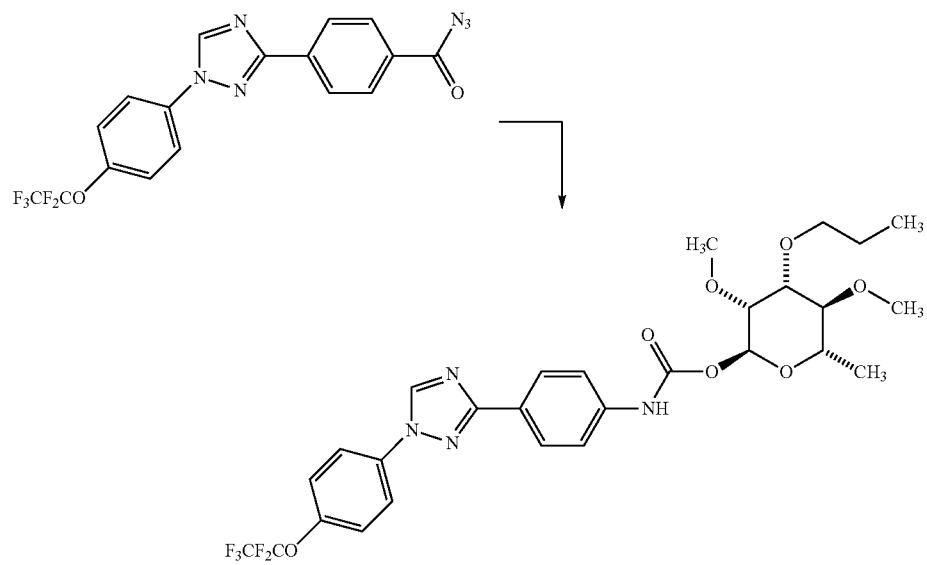

Into a 2-liter three-necked round bottom flask fitted with an overhead stirrer, nitrogen inlet, T-type K-Kem thermocouple, and reflux condenser was added 4-(1-(4-(perfluoroethoxy) phenyl)-1H-1,2,4-triazol-3-yl)benzoyl azide (26.2 g, 61.8 mmol) followed by anhydrous acetonitrile (300 mL). This gave a white suspension. To this suspension was added (3R, 4R,5S,6S)-3,5-dimethoxy-6-methyl-4-propoxytetrahydro-2H-pyran-2-ol (16.5 g. 70.4 mmol) which gave a white suspension. The suspension was heated with a mantle to 80° C. to give a pale yellow solution. The yellow solution was heated at an internal temperature of 82° C. for 2 hours. Analysis by LCMS showed complete conversion of the acyl azide. The heat source was removed and the reaction flask placed into an ice bath and cooled to 8.7° C. Cesium carbonate (10.5 g, 32.2 mmol) was added all at once and the reaction changed to a white-yellow suspension. The ice bath was removed and the reaction allowed to warm to 23° C. The progress of the reaction was monitored by LCMS. After 19 hours, the reaction appeared complete by LCMS. The reaction appearance was a yellow-white suspension. Water (1000 mL) was added slowly over 20 minutes. During the addition of the water, the reaction appearance first changed from a yellow-white suspension to a yellow solution and endothermed from 25° C. to 18° C. With the continued addition of water, the reaction appearance grew cloudy and a light-brown thick pasty precipitate formed. The reaction was stirred for an additional 30 minutes at 20° C. with no change. The reaction flask was placed into a heating mantle and the mixture heated to 60° C. for 2 hours. The precipitate changed slowly from a light brown paste to a light beige granular solid. After heating for 2 hours, the heat source was removed and the mixture allowed to return to 23° C. and stirred for 18 hours. This gave a light beige granular solid. The solid was collected by vacuum filtration. The solid was rinsed with water (2×50 mL) and the filtrate appearance was light yellow and a little cloudy. The solid was a beige very dense granule and the wet mass was 62.0 g (159% mass balance). The beige granules were placed into a vacuum oven (50° C., 72 cm Hg) for 8 hours until constant mass was achieved providing the title compound as beige granules (37.9 g, 97%): $^1$H NMR (400 MHz, CDCl$_3$) δ 8.56 (s, 1H), 8.16 (d, J=8.7 Hz, 2H), 7.81 (d, J=9.0 Hz, 2H),7.54 (d, J=8.1 Hz, 2H), 7.45-7.31 (m, 3H), 6.83 (s, 1H), 6.20 (d, J=1.9 Hz, 1H), 3.85-3.44 (m, 14H), 3.21 (t, J=9.4 Hz, 1H), 1.80-1.54 (m, 3H), 1.33 (d, J=6.2 Hz, 3H), 0.98 (t, J=7.4 Hz, 4H); $^{13}$C NMR (100 MHz, CDCl$_3$) 10.57, 17.88, 23.32, 59.21, 61.14, 70.40, 72.14, 76.73, 77.08, 77.44, 79.48, 81.47, 92.08, 118.70, 121.06, 123.04, 125.88, 127.49, 135.67, 138.78, 141.51, 147.49, 151.23, 162.95. $^{19}$F NMR (376 MHz, CDCl3) δ−87.8892, −85.9508; ESIMS m/z 632 ([M+H]$^+$).

Example 2

Preparation of (2S,3R,4R,5S,6S)-3,5-dimethoxy-6-methyl-4-propoxytetrahydro-2H-pyran-2-yl(4-(1-(4-(perfluoroethoxy)phenyl)-1H-1,2,4-triazol-3-yl)phenyl)carbamate

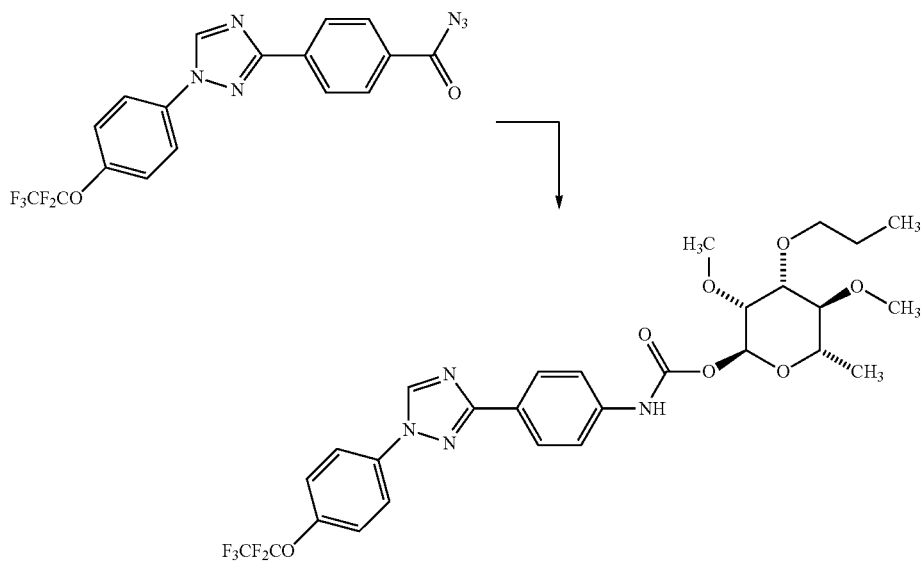

Into a 5-liter, three-neck flask, fitted with reflux condenser, nitrogen inlet, mechanical stirring, peristaltic pump inlet and thermocouple, was charged with (3R,4R,5S,6S)-3,5-dimethoxy-6-methyl-4-propoxytetrahydro-2H-pyran-2-ol (57.7 g, 246 mmol) in acetonitrile (1.0 L). The clear, colorless solution was heated to 80° C. and a 7% (w/w) solution of the acyl azide (100 g, 224 mmol) in toluene (1.5 L) was added dropwise via a peristaltic pump at a rate 15-20 mL/minute. The solution darkened to a light-brown color as material was added. During the addition the azide started to crystallize out of the toluene and 120 mL of 2-methyltetrahydrofuran was added to solubilize the material. The addition took 2 hours and 45 minutes to complete and the final temperature was 80° C. The solution was allowed to stir at 80° C. for 3 hours. The mixture was cooled to ambient temperature and analyzed by LCMS. The LCMS showed a 1:2 mixture of α:β anomers. Cesium carbonate (36.5 g, 112 mmol) was added and the suspension stirred for 16 hours. LCMS showed 98:2 α:β anomers.

After filtration, the mixture was concentrated on a rotary evaporator to ¼ volume, and heptane (1.5 L) was added and the mixture allowed to spin slowly, no vacuum, at 50° C. for 4 hours. The mixture was cooled to 25° C., vacuum filtered, and rinsed with heptane. This gave an off-white solid (113 g) and yellow filtrate.

The filtrate was stripped down to a brown oil/foam, taken up in methyl tert-butyl ether and heptane was added. The solution was placed on a rotary evaporator and the methyl tert-butyl ether was slowly pulled off under a gentle vacuum until crystallization was first noted. The vacuum was turned off and the flask was rotated slowly at 45° C. until complete precipitation was achieved. The mixture was cooled to 25° C. and the solid was filtered off, rinsed with a small amount of heptane and vacuum dried under a stream of nitrogen to yield an off-white solid (18.5 g) providing the title compound (131.5 g, 93%).

Example 3

Preparation of (2S,3R,4R,5S,6S)-3,5-dimethoxy-6-methyl-4-propoxytetrahydro-2H-pyran-2-yl(4-(1-(4-(perfluoroethoxy)phenyl)-1H-1,2,4-triazol-3-yl)phenyl)carbamate.

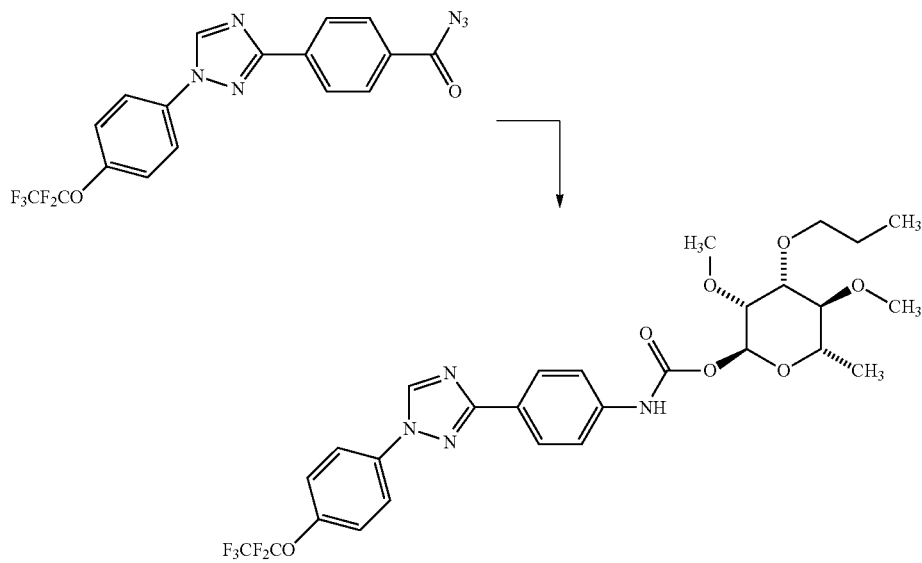

Into a 250 mL three-necked round bottom flask fitted with an overhead stirrer, nitrogen inlet, T-type J-Kem thermocouple, gas bubbler and reflux condenser was added anhydrous toluene (25 mL). The nitrogen flow rate into the reactor was set so that the gas bubbler showed about one bubble per second. The solvent was heated to 100° C. and a 5% (w/w) solution of 4-(1-(4-(perfluoro-ethoxy)phenyl)-1H-1,2,4-triazol-3-yl)benzoyl azide (5.05 g, 11.9 mmol) in toluene was slowly added over 2 hours. No exotherm was detected and no increase in gas evolution was observed during the addition. After the addition was complete, the resulting solution was heated for an additional 30 minutes. Analysis by LCMS indicated complete conversion of the acyl azide. The reaction was cooled to 25° C. and a solution of (3R,4R,5S,6S)-3,5-dimethoxy-6-methyl-4-propoxytetrahydro-2H-pyran-2-ol (3.07 g, 13.1 mmol) in anhydrous acetonitrile (50 mL) was added all at once. Powdered cesium carbonate (2.00 g, 6.00 mmol) was added all at once and this gave a white suspension. The suspension was stirred at 25° C. for 4 hours. The reaction mixture was poured into a separatory funnel containing water (50 mL). The phases were separated and the aqueous phase extracted with additional toluene (25 mL). The layers were separated and the toluene extracts were combined. The combined toluene extract was washed with brine (50 mL), dried over anhydrous sodium sulfate, filtered, and concentrated on a rotary evaporator to a volume of 20 mL. Heptane (100 mL) was added which gave a gelatinous precipitate. The mixture was stirred at 40° C. on a rotary evaporator (no vacuum) for 2 hours. This gave a white crystalline solid suspended in the organic layer. The solid was collected by vacuum filtration and rinsed with heptane (2×20 mL). This gave 7.3 g wet cake which was allowed to air dry to constant mass providing the title compound (6.3 g, 83%): mp=155-157° C.

Example 4

Preparation of 3-(4-isocyanatophenyl)-1-(4-(perfluoroethoxy)-phenyl)-1H-1,2,4-triazole

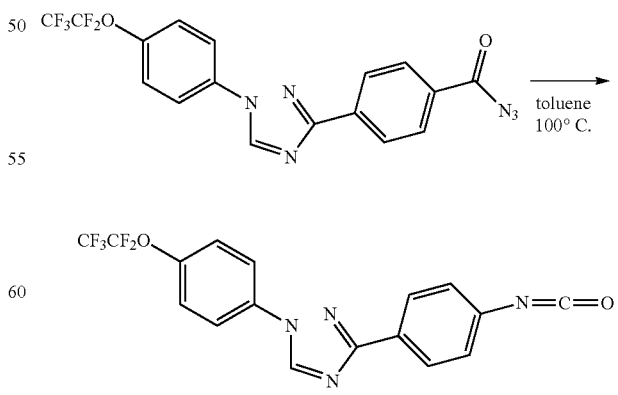

A 250 mL, three-neck flask, fitted with magnetic stirring, air condenser, temperature probe and nitrogen inlet, was charged with 4-(1-(4-(perfluoroethoxy)-phenyl)-1H-1,2,4-triazol-3-yl)benzoyl azide (5.00 g, 11.2 mmol) and toluene (100 mL). The brown solution was heated to 100° C. slowly and allowed to stir for 1 hour. Analysis of crude reaction mixture by LCMS shows the desired isocyanate. The reaction was cooled to 25° C. and the solvent removed by rotary evaporation to give a solid. The solid was dissolved in dichloromethane and the solution filtered to remove a small amount of a black insoluble material. The light-brown filtrate was rotary evaporated to yield 4.6 g of a tan solid. The solid was taken up in 30 mL of methyl tert-butyl ether, heated to effect a slightly turbid solution and filtered hot. The filtrate was re-heated to effect solution again and heptane (about 10-15 mL) was slowly added. The solution was placed on a rotary evaporator and the solvent was slowly removed under reduced pressure. When the first sign of solid was noted, the vacuum was broken and the mixture was allowed to slowly rotate at 40° C. to effect precipitation of solid. The solid was collected by vacuum filtration to give 3.4 g (77% yield) of a light tan solid, mp=119-121° C. $^1$H NMR (600 MHz, DMSO-$d_6$) δ 9.41 (s, 1H), 8.10-8.05 (m, 4H), 7.60 (d, J=8.7 Hz, 2H), 7.38 (dd, J=8.3, 1.6 Hz, 2H). $^{13}$C NMR (151 MHz, DMSO) δ 161.77, 146.66, 144.37, 136.23, 134.45, 128.26, 127.78, 125.91, 124.93, 123.57, 121.59.

What is claimed is:

1. A process for preparing triaryl rhamnose carbamates of the Formula (I),

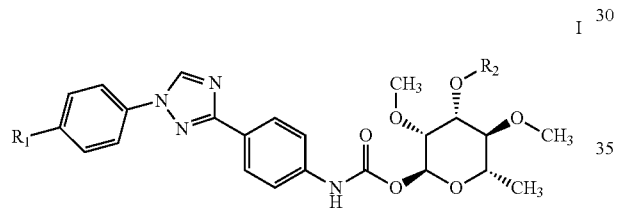

wherein
$R_1$ represents $(C_1-C_6)$haloalkyl or $(C_1-C_6)$haloalkoxy, and
$R_2$ represents $(C_1-C_6)$alkyl, $(C_2-C_6)$alkenyl or $(C_2-C_6)$alkynyl,
which comprises
a) rearranging a triaryl acyl azide of Formula (II)

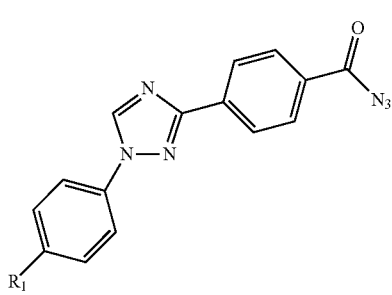

wherein
$R_1$ is as previously defined,
to an isocyanate of Formula (III)

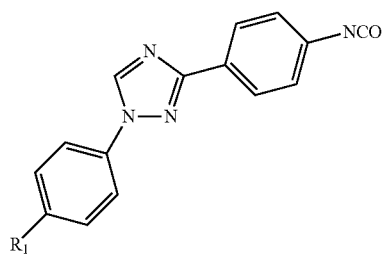

wherein
$R_1$ is as previously defined,
by heating at a temperature of about 60° C. to about 110° C. in an anhydrous aprotic solvent, and b) contacting the isocyanate of Formula (III) with a tetrahydropyran-2-ol of Formula (IV)

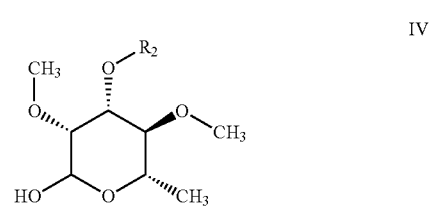

wherein
$R_2$ is as previously defined,
in a polar aprotic solvent in the presence of cesium carbonate.

2. The process of claim 1 in which $R_1$ is a $(C_1-C_2)$fluoroalkoxy group.

3. The process of claim 1 in which $R_2$ is $CH_2CH_3$, $CH_2CH_2CH_3$ or $CH_2CH=CH_2$.

4. The process of claim 1 in which the isocyanate of Formula (III) is prepared and used in situ.

5. The process of claim 1 or 4 in which the anhydrous aprotic solvent and the polar aprotic solvent are a mixture of an aromatic hydrocarbon and a nitrile.

6. The process of claim 5 in which the anhydrous aprotic solvent and the polar aprotic solvent are a mixture of toluene and acetonitrile.

* * * * *